United States Patent
Kurkov

[11] 4,031,114
[45] June 21, 1977

[54] ALPHA, BETA-BUTENOLIDE PREPARATION

[75] Inventor: Victor P. Kurkov, San Rafael, Calif.

[73] Assignee: Chevron Research Company, San Francisco, Calif.

[22] Filed: Mar. 29, 1976

[21] Appl. No.: 671,881

[52] U.S. Cl. .......................................... 260/343.6
[51] Int. Cl.² .................................... C07D 307/32
[58] Field of Search ................................ 260/343.6

[56] References Cited
OTHER PUBLICATIONS

Palm, et al., Chem. Abs. 66: 55835u (1967).
Franck–Neumann et al., Chem. Abs. 70: 46784g (1969).

*Primary Examiner*—Cecilia M. S. Jaisle
*Attorney, Agent, or Firm*—Dix A. Newell; John Stoner, Jr.; W. Keith Turner

[57] ABSTRACT

A method for preparing an alpha,beta-dehydro-gamma-butyrolactone which comprises contacting a carboxylic acid of the formula

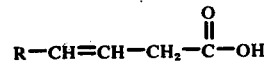

wherein R is H or $C_1$ to $C_{10}$ alkyl group, with oxygen and a catalyst comprising a noble metal halide, a variable valence transition metal halide and an alkali metal halide at a temperature between 50° and 300° C and superatmospheric pressure.

8 Claims, No Drawings

ALPHA, BETA-BUTENOLIDE PREPARATION

BACKGROUND OF THE INVENTION

The present invention is directed to the preparation of alpha,beta-dehydro-gamma-butyrolactone which, in turn, can be converted to gamma-butyrolactone by hydrogenation of the double bond. The alpha,beta-unsaturated lactone is useful as a solvent or monomer but, more particularly, upon hydrogenation the resulting gamma-butyrolactone is valuable to make the corresponding lactam as by reaction with ammonia. The lactam can be used to make fibers such as nylon fibers.

Previously gamma-butyrolactone has been made by converting gamma-hydroxycarboxylic acids to the lactone as follows:

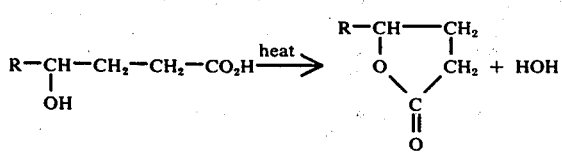

See, for example, Cason, *Principles of Modern Organic Chemistry*, Prentice-Hall, Inc., 1966.

Morrison and Boyd, *Organic Chemistry*, 2nd Ed., Allyn and Bacon, Inc., Boston, 1970, give the reaction as follows for the salt of a gamma-hydroxy acid:

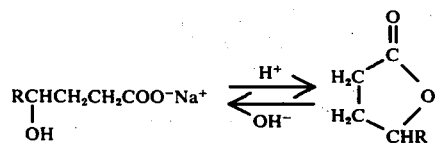

Commercially gamma-butyrolactone is made from 1,4-butanediol by oxidative cyclization. However, the diol is believed to first be converted to the hydroxy acid before the cyclization occurs so that the cyclization would be as given in the above equations.

Previous methods of making alpha,beta-dehydro-gamma-butyrolactone, which may also be referred to as alpha,beta-butenolide, include a multistep process in which 3-butenoic acid is first converted into the corresponding epoxide by reaction with performic acid; the epoxide is then treated with hydrochloric acid to effect cyclization to a hydroxylactone, and finally this hydroxylactone is dehydrated over polyphosphoric acid to the unsaturated lactone. R. Palm, H. Ohse, and H. Cherdon Angew. Chem. Int. Ed. Engl. 5, (12), 994 (1966).

SUMMARY OF THE INVENTION

According to the present invention a method is provided for preparing an alpha,beta-dehydro-gamma butyrolactone which comprises contacting a carboxylic acid of the formula

wherein R is H or $C_1$ to $C_{10}$ alkyl group, with oxygen and a catalyst comprising a noble metal halide, a variable valence transition metal halide and an alkali metal halide at a temperature between 50° and 300° C and superatmospheric pressure.

Preferred operating conditions for the method of the present invention are as follows:

|  | Preferred | More Preferred | Most Preferred |
|---|---|---|---|
| Temperature, ° C | 50–175 | 50–150 | 75–125 |
| Pressure, atm. | .1–100 | 5–30 | 7–20 |
| Oxygen partial pressure, atm. | .1–100 | 1–25 | 5–20 |
| Feed | — | — | 3-butenoic acid |
| Solvent | organic acids nitriles 3° amides | 3-butenoic acid benzonitrile | 3-butenoic acid |
| Catalyst (e.g. Pd or Pt/Cu/Li) | ↑ sulfoxides | ↑ dimethyl-acetamide |  |
| $PdCl_2$, $PtCl_2$ mol % | .01–10 | 0.5–5 | 1–5 |
| $CuCl_2$ mol % | .1–40 | 3–30 | 5–25 |
| LiCl mol % | .1–50 | 5–40 | 10–30 |

The term "noble metal catalyst" is used herein to mean ruthenium, rhodium, palladium, osmium, iridium and platinum. Palladium and platinum are particularly preferred noble metal catalysts for the present preparation method.

The term "variable valence transition metals" is used herein to mean those transition metals which can change their valence by state of oxidation-reduction more specifically metals, which can be oxidized to their higher oxidation state by air or oxygen. Preferred transition metal catalysts are copper and iron. Particularly preferred as the transition metal catalyst is copper, especially as $CuCl_2$.

The term "alkali metal" is used herein to mean Group IA metals. Of these metals lithium, sodium, and potassium are preferred and lithium is especially preferred.

One unexpected aspect of the present invention is that the cyclization reaction appears to occur in an anti-Markovnikov fashion, although the present invention is not to be limited by the hypothesized method for the reaction. The reaction equation is indicated as follows for the 3-butenoic acid feed:

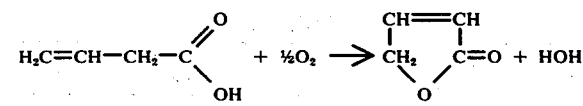

In the above equation the cyclization reaction appears to occur by a route wherein the carboxyl oxygen is attached to the terminal carbon atom, which has more hydrogen atoms than does the internal double bond carbon atom. In a Markovnikov-type addition the negatively charged carboxyl oxygen would be expected to attach to the internal carbon atom similar to the reaction of hydrogen bromide with propylene wherein 2-bromo-propane is formed according to the normal Markovnikov reaction with the negatively charged bromide group going to the internal double bond carbon atom, which has fewer hydrogen atoms than does the terminal doubly bonded carbon atom.

My concurrently filed and related application Ser. No. 671,880 titled "4-Pentenoic Acid Conversion", illustrates a reaction wherein a lactone is formed with the carboxyl group attaching to the internal carbon atom in what may be regarded as a normal Markovnikov addition position for the cyclization reaction.

EXAMPLES

As indicated in the Tables below, butenoic acid, solvent and catalyst were charged into a glass pressure reactor provided with a magnetic stirrer. The catalyst was a homogeneous catalyst in the liquid phase. The reactor was connected to a gas reservoir through a pressure regulator. Sufficient oxygen was added to bring the pressure to 100 psig, and the reactants were then heated to the reaction temperature. The pressure was adjusted to the desired value and the reaction continued at constant pressure.

Upon completion, the reactor was depressured and the products analyzed by gas chromatography. When two phases were present tetrahydrofuran was added prior to analysis.

Alpha,beta-butenolide was separated out by distillation and identified by spectral comparison with an authentic sample prepared by the procedure of R. Palm et al, Angew, Chem. Int. Ed., Engl., 5 (12), 994 (1966). The data summarized in Tables I through V illustrates that yields of 40 to 50 mol % and higher of alpha,beta-butenolide can be achieved using the process of the present invention. Run No. 18 in Table V also illustrates that, if desired, the reaction can be carried out in the absence of oxygen gas by using lithium acetate and a stoichiometric amount of cupric chloride.

TABLE I

| Run No. | $PdCl_2$ mmol | Time Hr. | Conv. % | Yield mol % | Id. No. |
|---|---|---|---|---|---|
| 1 | 1.15 | 1 | 88.8 | 34.5 | B2066-24 |
| 2 | 2.4 | 1 | 76.6 | 40.3 | B2066-05 |
| 3 | 4.6 | 1 | 94.1 | 44.3 | B2066-20 |
| 4 | 9.2 | 1 | 92.6 | 47.8 | B2066-22 |
| 5 | 18.0 | 1 | 84.2 | 34.4 | B2102-22 |

Charge:
3-Butenoic Acid    100 mmol
Toluene    32.6 "
LiCl    30.2 "
$CuCl_2$    19.9 "
$PdCl_2$    as shown
Temperature = 100° C
Pressure = 100 psig $O_2$

TABLE II

| Run No. | $CuCl_2$ mmol | Time Hr. | Conv. % | Yield mol % | Id. No. |
|---|---|---|---|---|---|
| 6 | 5 | 1 | 69.3 | 17.9 | B2066-06 |
| 7 | 10 | 1 | 61.8 | 34.3 | B2009-33 |
| 8 | 20 | 1 | 76.6 | 40.3 | B2066-05 |
| 9 | 20 | ½ | 35.4 | 34.2 | B2066-09 |
| 10 | 38 | 1 | 71.3 | 34.2 | B2066-08 |

Charge:
3-Butenoic Acid    100 mmol
Toluene    32.6 "
LiCl    30.2 "
$CuCl_2$    as shown
$PdCl_2$    2.4 mmol
Temperature = 100° C
Pressure = 100 psig $O_2$

TABLE III

| Run No. | $PdCl_2$ mmol | $CuCl_2$ mmol | Solvent ml | Time Hr. | Conv. % | Yield mol % | Id. No. |
|---|---|---|---|---|---|---|---|
| 11 | 9.5 | 60.2 | Benzonitrile 50 | 1 | 91.4 | 56.1 | B2066-43 |
| 12 | 9.4 | 20.0 | Benzonitrile 50 | 1 | 81.4 | 26.0 | B2066-44 |
| 13 | 18.2 | 20.0 | — | ½ | 73.5 | 30.1 | B2066-39 |
| 14 | 18.2 | 60.4 | — | ½ | 76.5 | 29.3 | B2066-41 |

Charge:
3-Butenoic Acid    90 mmol    Solvent as shown
Toluene    32 "    Temperature = 100° C
LiCl    30 "    Pressure = 100 psig $O_2$
$PdCl_2$, $CuCl_2$    as shown

TABLE IV

| Run No. | Catalyst | $CuCl_2$ mmol | Solvent ml | Time Hr. | Conv. % | Yield mol % | Id. No. |
|---|---|---|---|---|---|---|---|
| 15 | $KPtCl_4$ 1 mmol | 20 | — | 2 | 12.2 | 93.2 | B2066-50 |
| 15a | | | | 16 | 87.2 | 33.3 | |
| 16 | $PtCl_2$ 2.4mmol | 20 | — | 2 | 38.6 | 53.9 | B2102-08 |
| 17 | $PdCl_2$ 2.4mmol | 20 | — | 1 | 76.6 | 40.3 | B2066-05 |

Charge:
3-Butenoic Acid    90 mmol    Solvent as shown
Toluene    32 "    Temperature = 100° C
LiCl    30 "    Pressure = 100 psig $O_2$
Catalyst as shown

TABLE V

| Run No. | Catalyst (mmol) | Temp °C | Time Hr. | Conv. % | Yield mol % | Id. No. |
|---|---|---|---|---|---|---|
| 18 | $PtCl_2$ (2.3)-$CuCl_2$ (116)-LiOAc(130) | 100 | 2 | 61.8 | 50.7 | B2231-16[1] |
| 18a | | | 4 | 80.9 | 48.9 | B2231-16[1] |
| 19 | $PtCl_2$ (2.3)-$CuCl_2$ (116)-LiCl (60) | 100 | 2 | 30.8 | 0 | B2231-13[1] |
| 20 | $PtCl_2$ (2.3)-$CuCl_2$ (30.5)-LiOAc (15) | 100 | 3 | 66.4 | 42[4] | B2163-44 |
| 21 | $PtCl$ (2.3)-$CuCl_2$ (30.5)-LiOAc(15) | 100 | 3 | 79.7 | 30.8 | B2163-45 |
| 22 | $PtCl_2$ (2.3)-$CuCl_2$ (30.5)-LiCl (15) | 100 | 3 | 100.0 | 45.5[2] | B2163-49 |
| 23 | $PtCl_2$ (2.3)-$CuCl_2$ (30.5)-LiCl (60) | 100 | 2 | 100.0 | 45.0 | B2231-10 |
| 24 | $PtCl_2$ (2.3)-$CuCl_2$ (30.5)-LiCl (15)-LiOAc (15) | 100 | 2.5 | 86.2 | 49.1[2] | B2231-06 |
| 25 | $PtCl_2$ (2.3)-$CuCl_2$ (10)-LiCl (15)-LiOAc (15) | 100 | 2.5 | 64.7 | 32.5 | B2231-16 |
| 26 | $PtCl_2$ (2.3)-$CuCl_2$(30.5)-LiCl (30) | room temp | 88 | 9.0 | 0 | B2231-09 |

Charge:
3-Butenoic Acid    58 mmol
HOAc    25 ml
Toluene    32 mmol
Catalyst as shown Pressure = 100 psig $O_2$ (unless otherwise indicated)
[1]Under 100 psig $N_2$
[2]Includes small amount of crotonic acid

TABLE VI

| Run No. | Temp., °C | Time, hrs. | Conv., % | Yield, % | Id. No. |
|---|---|---|---|---|---|
| 27 | 60 | 2 | 100 | 34.5 | B2102-18 |
| 28 | 80 | 1 | 41.3 | 36.2 | B2102-16 |
| 28a | 80 | 2 | 100 | 33.0 | — |
| 29 | 100 | 1 | 91.4 | 56.1 | B2066-45 |
| 30 | 120 | .5 | 90 | 42 | B2102-34 |
| 31 | 60 | 2 | 100 | 34.5 | B2102-13 |
| 31a | 60 | 3 | 100 | 38.6 | — |
| 32 | 40 | .67 | 87.3 | 39.8 | B2102-38 |
| 32a | 100 | 1 | 100 | 52.1 | — |

Charge:
| | | |
|---|---|---|
| 3-butenoic acid | 88 | mmol |
| benzonitrile | 50 | ml |
| toluene | 32 | mmol |
| LiCl | 30 | mmol |
| CuCl$_2$ | 60 | mmol |
| PdCl$_2$ | 9.4 | mmol |

TABLE VII

| Run No. | Catalyst | Time, hrs. | Conv., % | Yield, % | Id. No. |
|---|---|---|---|---|---|
| 33 | PdCl$_2$ | 2 | 20 | 58.4 | B2102-27 |

Charge:
| | | |
|---|---|---|
| PdCl$_2$ | 20 | mmol |
| 3-butenoic acid | 80.5 | mmol |
| benzonitrile | 50 | ml |
| toluene | 32.2 | mmol |
| oxygen | none | |
| nitrogen | 100 | psig |
| Temperature | 100° C | |

Run No. 33 was carried out using a stoichiometric amount of PdCl$_2$, that is, 20.5 mmol, and using no oxygen. In this method of operation, the 3-butenoic acid was oxidized to the product lactone, and the PdCl$_2$ was reduced to Pd and HCl. In the presence of HCl, the Pd could be oxidized back to PdCl$_2$ in a separate reaction zone in the presence of copper chloride using air or oxygen.

However, as shown by the conversion and yield in Table VII, I found that in this method of operation relatively low amounts of the product lactone were obtained, compared to operation in accord with the present invention.

What is claimed is:

1. A method for preparing an alpha,beta-dehydro-gamma-butyrolactone which comprises contacting a carboxylic acid of the formula

wherein R is H or C$_1$ to C$_{10}$ alkyl group, with oxygen and a catalyst comprising a noble metal halide, a copper or iron halide and an alkali metal halide at a temperature between 50° and 300° C and superatmospheric pressure.

2. A process in accordance with claim 1 wherein the temperature is 75° to 150° C.

3. A process in accordance with claim 2 wherein the halide is chloride and wherein the noble metal is platinum or palladium, the transition metal is copper, and the alkali metal is lithium.

4. A process in accordance with claim 3 wherein the reaction is carried out in the presence of an inert hydrocarbon solvent.

5. A process in accordance with claim 4 wherein the solvent is 3-butenoic acid.

6. A process in accordance with claim 3 wherein the carboxylic acid feed is 3-butenoic acid.

7. A process in accordance with claim 3 wherein the catalyst comprises 0.1 to 10 parts platinum or palladium chloride, 1 to 40 parts cupric chloride, and 1 to 50 parts lithium chloride wherein the parts are on a molar basis.

8. A process in accordance with claim 1 wherein the halide is chloride.

* * * * *